United States Patent [19]

Jackson et al.

[11] Patent Number: 5,281,693

[45] Date of Patent: * Jan. 25, 1994

[54] ISOLATION OF SPIDER TOXINS

[75] Inventors: J. R. Hunter Jackson; Thomas N. Parks, both of Salt Lake City, Utah

[73] Assignee: University of Utah Research Foundation, Salt Lake City, Utah

[*] Notice: The portion of the term of this patent subsequent to May 15, 2007 has been disclaimed.

[21] Appl. No.: 523,797

[22] Filed: May 15, 1990

Related U.S. Application Data

[63] Continuation-in-part of Ser. No. 921,218, Oct. 20, 1986, Pat. No. 4,925,664.

[51] Int. Cl.$^5$ .............................................. C07K 13/00
[52] U.S. Cl. ..................................... 530/324; 530/855
[58] Field of Search ........................... 530/324; 514/12; 435/69.1

[56] References Cited

U.S. PATENT DOCUMENTS

| | | | |
|---|---|---|---|
| 4,925,664 | 5/1990 | Jackson et al. | 424/537 |
| 4,950,739 | 8/1990 | Cherskey et al. | 530/350 |
| 5,122,596 | 6/1992 | Phillips et al. | 530/350 |

FOREIGN PATENT DOCUMENTS 0156540  3/1985  European Pat. Off. .

OTHER PUBLICATIONS

Skinner et al. "Purification and Characterization of Two Classes of Neurotoxins from the Funnel Web Spider, *Agelenopsis aperta* "J. Biol. Chem. v. 264 (4) pp. 2150–2155 Feb. 5, 1989.

Abe, T. et al., "Effects of a Spider Toxin on the Glutaminergic Synapse of Lobster Muscle", J. Physiol. (Lond.) 339–252 (1983).

Adams, Michael E. et al., "Isolation and Biological Activity of Synaptic Toxins from the Venom of the Funnel Web Spider, *Agelenopsis aperia.*"

Adams, M. E. et al., "Multiple Synaptic Antagonists from the Venom of an Orb Weaver Spider," Society for Neuroscience Abstracts, paragraph 260.2, p. 946 (1986).

Bachmann, M., "Isolation and Partial Characterization of a Toxin from the Venom of the East African Orthognath Spider *pterinochilus* Spec.", Toxicon 20:547–552 (1982).

Bateman, A. et al., "Postsynaptic Block of a Glutamatergic Synapse by Low Molecular Weight Fractions of Spider Venom," 339 Brain Research, 237 (1985).

Bowers, C. W. et al., "Isolation and Partial Characterization of a New Irreversible Presynaptic Neurotoxin from Spider Venom," Society of Neuroscience Abstracts 12:27 (1986).

Bowers, C. W. et al., "Identification and Purification of an Irreversible Presynaptic Neurotoxin from the Venom of the Spider *Hololena curta*," Proc. Natl. Acad. Sci. USA, 84:3506–3510 (May 1987).

Branton, W. D. et al., "New Presynaptic Neurotoxins from Spider Venom," Society of Neuroscience Abstracts 12:176 (1986).

Croucher, J. J. et al., "Anticonvulsant Action of Excitatory Amino Acid Antagonists," Science 216:899–901 (1982).

Cruz-Hofling, M. A. et al., "Effects of *Phoneutria Nigriventer* Spider Venom on Mouse Peripheral Nerve," Quart. J. Exp. Physiol. 70:623–640 (1985).

Duchen, L. W. et al., "The Pharmacology of Spider Venoms," In: A. T. Tu (Ed.), Insect Poisons, Allergens and Other Invertebrate Venoms. Handbook of Natural Toxins, vol. 2, New York M. Dekker, pp. 483–513 (1984).

Entwistle et al., "Isolation of a Pure Toxic Polypeptide from the Venom of the Spider *Phoneutria Nigriventer* and its Neurophysiological Activity on an Insect Femur Preparation," Toxicon 20:1059–1067 (1982).

Foil, L. D. et al., "Partial Characterization of Lethal and Neuroactive Components of the Brown Recluse Spider (*Loxosceles reclusa*) Venom," Toxicon 17:347–354 (1979).

Geren, C. R. et al., "The Biochemistry of Spider Venoms,"In: A. T. Tu (Ed.), Insect Poisons, Allergens and Other Invertebrate Venoms. Handbook of Natural Toxins, vol. 2, New York, M. Dekker, pp. 441–481 (1984).

Greenamyre, J. T., "The Role of Glutamate in Neurotransmission and in Neurologic Disease,"Archives of Neurology 43:1058–1063 (1986).

Jackson H. et al., "Non-N-Methyl-D-Aspartate Receptors Mediating Synaptic Transmission in the Avian Cochlear Nucleus: Effects of Kynurenic Acid, Dipicolinic Acid and Streptomycin," 16 Neuroscience, 171 (1985).

Jackson, H. et al., "Spider Venoms Block Synaptic Transmission Mediated by Non-N-Methyl-D-Aspartate Receptors in the Avian Cochlear Nucleus," presented to the Society for Neuroscience Oct. 21, 1985.

Jackson, Hunter et al., "Presynaptic Blockade of Transmission by a Potent Long-Lasting Toxin from *Aglenopsis Aperta* Spiders," Society for Neuroscience Abstracts 12:730 (1986).

Jackson, Hunter et al., "Effects of Spider Venoms on Transmission Mediated by Non-N-Methyl-D-Aspartate Receptors in the Avian Cochlear Nucleus," In: T. P. Hicks et al. Excitatory Amino Acid Transmission, New York, A. R. Liss, pp. 51–54 (1987).

Kawai, Nobufumi et al., "Spider Venom Contains Specific Receptor Blocker of Glutaminergic Synapses," 247 Brain Research, 169 (1982).

Kawai, Nobufumi et al., "Effect of a Spider Toxin on Glutaminergic Synapses in the Mammalian Brain," 3 Biomedical Research, 353 (1982).

Kawai, Nobufumi et al., "Block of Glutamate Receptors by a Spider Toxin," (1983).

Kawai, Nobufumi et al., "Blockade of Synaptic Transmission in the Squid Giant Synapse by a Spider Toxin (JSTX)," 278 Brain Research, 346 (1983).

Kawai, Nobufumi et al., "Spider Toxin (JSTX) on the Glutamate Synapse," 79 J. Physiol., Paris, 228 (1984).

Love, S. et al., "Morphological Abnormalities in Myelinated Nerve Fibers Caused by Leiurus, Centriuoides and Phoneutria Venoms and Their Prevention by Tetrodotoxin," Quart. J. Exp. Physiol. 71:115–122 (1986).

Meldrum, B., "Excitatory Amino Acids and Anoxic/Ischaemic Brain Damage," Trends Neuroscience 8:47–48 (1985).

Michaelis, E. K. et al., "Spider Venoms Inhibit L--Glutamate Binding to Brain Synaptic Membrane Receptors," 81 Proc. Natl. Acad. Sci. USA, 5571 (Sep. 1984).

Miller, R. J., "Toxin Probes for Voltage Sensitive Calcium Channels," Trends in Neuroscience 7:309 (1984).

Miller, R. J., "Multiple Calcium Channels and Neuronal Function," Science 235:46–52 (1987).

Nagai, Takatoshi et al., "Differential Blocking Effects of a Spider Toxin on Synaptic and Glutamate Responses in the Afferent Synapse of the Acoustico-lateralis Receptors of Plotosus," 300 Brain Research, 183 (1984).

Nemeth, E. F. et al., "Pharmacological Evidence for Synaptic Transmission Mediated by Non-N-Methyl-D-Aspartate Receptors in the Avian Cochlear Nucleus," 40 Neuroscience Letters, 39 (1983).

Nemeth, E. F. et al., "Evidence for the Involvement of Kalnate Receptors in Synaptic Transmission in the Avian Cochlear Nucleus," 59 Neuroscience Letters, 297 (1985).

Odell, G. V. et al., "A Review of Research on Tarantula Colony Maintenance, Venom Collection, Composition and Toxicity."

Quicke, Donald L. J. et al., "Postsynaptic Blockade of Locust Neuromuscular Transmission by Low Molecular Weight Fractions of Araneid Venoms," presentation made at Spider Venom Satellite Symposium held in Jun. 1986.

Rees, Riley et al., "Clinical Treatment of Confirmed Brown Recluse Spider Bites with Dapsone and Antivenom."

Rothman, S. M. et al., "Glutamate and the Pathophysiology of Hypoxic-Ischemic Brain Damage," Annals of Neurology 19:105–111 (1986).

Saito, Mitsuyoshi et al., "Spider Toxin (JSTX) Blocks Glutamate Synapse in Hippocampal Pyramidal Neurons," 346 Brain Research, 397 (1985).

Schwarcz et al., "Excitatory Amino Acid Antagonists Provide a Therapeutic Approach to Neurologic Disorders," The Lancet, Jul. 20, 140–143 (1985).

Sheumack et al., "A Comparative Study of Properties and Toxic Compounds of Funnel Web Spider (Atrax) Venom," Comp. Biochem. Physiol. 78C:55–56 (1984).

Sperelakis, N., "Properties of Calcium-Dependent Slow Action Potentials: Their Possible Role in Arrhythmias," In: L. H. Opie (Ed.), Calcium Antagonists and Cardiovascular Disease, New York, Raven Press, pp. 277–291 (1984).

Sperelakis, N. et al., "Properties of Myocardial Calcium Show Channels and Mechanisms of Action of Calcium Antagonistic Drugs," Current Topics in Membrane and Transport, 25:44–76 (1985).

Tashmukhamedov, B. A. et al., "Effects of Different Spider Venoms on Artificial and Biological Membranes," Toxins as Tools in Neurochemistry (1983).

Tashmukhamedov, B. A., "Reconstitution in Bilayer Lipid Membranes of the Crab Potamon Transcaspicum Spider Venom Sensitive Glutamate Receptors," 4 Gen. Physiol. Biophys., 625 (1985).

Tzeng, Mu-Chin et al., "Chemistry and Actions of a-Latrotoxin from Black Widow Spider Venom."

Usherwood, Peter N. R. et al., "Slowly-reversible Block of Glutamate Receptor-Channels by Venoms of the Spiders, *Argiope trifasciata* and *Araneus gemma*," 79 J. Physiol., Paris, 241 (1984).

Usherwood, Peter N. R. et al., "Antagonism of Glutamate Receptor Channel Complexes by Spider Venom Polypeptides," 6 NeuroToxicology 239 (1985).

Usmanov, P. B. et al., "Study of the Effect of Lityphantes Payukullianus Spider Venom on Synaptic Processes," Biol. Nauki (Moscow) 9:23-28 (1982).

Usmanov, P. B. al., "Action of Venom of the Spider *Argiope lobato* on the Glutamatergic and Cholinergic Synapses," (1984).

Volkova, T. M. et al., "Structural Characteristic of Argiopine-Blocker of Glutamate Channels from the Venom of Spider *Argiope Lobata*," presented at the Sixth European Society for Neurochemistry General Meeting in Prague (1986).

Vyklicky, Ladislav, Jr. et al., "Spider Venom of Araneus Opens and Desensitizes Glutamate Channels in Chick Spinal Cord Neurones," 68 Neuroscience Letters, pp. 227-231 (1986).

Vyklicky, L., Jr. et al., "Araneus Spider Venom Opens and Desensitizes Glutamate Channels in Chick Spinal Cord Neurones," presented at the Sixth European Society for Neurochemistry General Meeting in Prague (1986).

Watkins, J. C., "Excitatory Amino Acids and Central Synaptic Transmission," Trends in Pharmacological Sciences, Sep. (1984).

Young, E. F. et al., "Neurotoxic Action of the Venom of the Common American House Spider," Physiol. Zool. 57:521-529 (1984).

*Primary Examiner*—Robert J. Hill, Jr.
*Assistant Examiner*—Nina Ossanna
*Attorney, Agent, or Firm*—Workman, Nydegger & Jensen

[57] ABSTRACT

Methods and compositions for blocking $Ca^{2+}$ channels within an organism are provided. For example, a toxin was isolated from the *Agelenopsis aperta* spider. The toxin comprised a 48 amino acid toxin having a molecular weight of approximately 5,274. This toxin was found to block calcium channels within the central nervous system. The Agelenopsis gene responsible for producing this toxin has been identified and cloned. This gene and/or its derivatives provide a mechanism by which the toxin can be produced using recombinant DNA expression technologies.

The present invention further relates to methods of treating neurological diseases by applying the toxins isolated and identified. The toxin may provide beneficial effects on certain neurological conditions including seizures, ischemic-hypoxic CNS damage, and neurodegenerative disorders. It is also found that the toxins are effective as tags in probing calcium channels.

8 Claims, 2 Drawing Sheets

ISOLATION OF SPIDER TOXINS

RELATED APPLICATION

This application is a continuation in part of applicant's copending application Ser. No. 06/921,218, filed Oct. 20, 1986, now U.S. Pat. No. 4,925,664, entitled "Spider Toxins and Methods for their Use as Blockers of Calcium Channels and Amino Acid Receptor Function," which application is incorporated herein by reference.

BACKGROUND

1. The Field of the Invention

The present invention generally relates to the isolation of certain toxins from spider venoms and the use of those toxins as inhibitors of the functions of ion channels. In particular, the present invention relates to spider venom toxins and their use as blockers of calcium channels in the central nervous and neuromuscular systems of organisms, including humans.

2. The Background of the Invention

Movement of calcium ions across cell membranes is a critically important event in the normal functioning of excitable tissues such as vascular smooth muscle, cardiac muscle, and the central nervous system. Influx of calcium ions through specialized channels in the cell membranes regulates release of substances such as hormones and neurotransmitters.

The movement of calcium ions also regulates contraction of heart muscle and of vascular smooth muscle in the wall of blood vessels. Abnormal influx of calcium ions has been reported to play a role in the pathogenesis of various cardiovascular disorders (e.g., anoxic/ischemic heart disease), and drugs capable of blocking the movement of calcium through calcium channels have been used for treatment of cardiac arrhythmias, coronary artery disease, and cardiomyopathy.

The currently used drugs, however, have nonspecific physiological effects and varying tissue specificities that can lead to undesirable side-effects in patients. Moreover, there are several known subtypes of calcium channels with varying physiological actions and no drug that specifically blocks certain of these subtypes is known.

In the nervous system, calcium influx into the presynaptic nerve terminal via calcium channels is a necessary prerequisite for the release of chemical neurotransmitter at synapses and thus for the proper functioning of these synapses. Lowering of the extracellular calcium concentration is routinely used by neurophysiologists to reduce or abolish synaptic transmission in isolated pieces of nervous tissue.

It has not been possible, however, to specifically affect synaptic transmission in vivo in the central nervous system ("CNS") by manipulating the function of neuronal calcium channels. With the exception of the omega-conotoxin recently isolated from the venom of the marine snail *Conus geographus*, no drug with sufficiently specific or potent effects on CNS calcium channels is known.

Abnormal influx of calcium is thought to be very important in the pathogenesis of several CNS disorders, including anoxic/ischemic (stroke) damage, epilepsy, and the neuronal death associated with chronic epilepsy. Again, the paucity of chemical agents that potently and specifically block CNS calcium channels has impeded the development of an effective drug therapy for these prevalent neurological problems.

Thus, it would be a very considerable improvement in the art if it were possible to develop chemical agents that specifically and potently block calcium channel function in the CNS. In particular, it would be an advancement in the art to provide a specific blocker for particular subtypes of calcium channel. Similarly, it would be an advancement in the art to provide a specific blocker of calcium channels in the CNS.

Such chemical compositions and methods for their use are disclosed and claimed below.

BRIEF SUMMARY AND OBJECTS OF THE INVENTION

The present invention is related to the isolation, identification, and use of spider venoms and toxins contained within these venoms. In particular, the present invention is related to the isolation and use as calcium channel blockers of certain toxins from spider venom.

As discussed above, calcium channels are intimately involved in the functions of the cardiovascular system since calcium influx affects contraction of cardiac muscle and vascular smooth muscle. Similarly, calcium influx into nerve cells is required for the release of chemical neurotransmitter substances at synapses and, therefore, for the normal functioning of the nervous system. Calcium influx into nerve cells is also involved in mediating certain electrical responses of those cells. Abnormal calcium influx into cells is associated with serious cardiovascular and neurological disorders.

The present invention is related to obtaining toxins from spider venoms, which toxins have specific and potent blocking effects on calcium channels within the organism.

Within the scope of the present invention, spider venom is obtained by milking spiders of various species. That is, the spider venom is obtained by electrical stimulation of the spider to cause release of the venom and subsequent suction in order to collect the released venom. This assures that impurities, which have traditionally been contained within spider venoms obtained by conventional techniques, are eliminated.

Spider venoms are known to be a complex mixture of enzymes, peptide toxins, nucleotides, free amino acids, and other molecules. As a result, in order to obtain useful spider toxins it is necessary to separate the various components of the whole spider venom. According to one embodiment of the present invention, whole venoms are fractionated by gel filtration to separate components of the venom by relative molecular mass. It will be appreciated, however, that any type of fractionation technique or other technique may be useful to obtain the spider venom toxins necessary for use in the present invention.

A group of specific spider venoms has been isolated and used extensively in the context of the present invention. The spiders that have been used within the scope of the present invention are *Agelenopsis aperta* spiders. Agelenopsis spiders are members of the funnel-web grass spider family Agelenidae and are commonly found in meadows and other grassy areas within the western United States.

The primary specific toxin which falls within the scope of the present invention has been isolated from the Agelenopsis spider. In particular, a relatively high molecular weight toxin that suppresses synaptic transmission in the vertebrate central nervous system by blocking calcium channels. For ease of identification this toxin will be sometimes generally referred to as "AG1" during the present description of the invention.

AG1 has been identified by amino acid sequencing techniques as a 48 amino acid peptide. The toxin is found to have the following sequence:

Glu—Asp—Asn—Cys—Ileu—Ala—Glu—Asp—Tyr—Gly—

Lys—Cys—Thr—Trp—Gly—Gly—Thr—Lys—Cys—Cys—

Arg—Gly—Arg—Pro—Cys—Arg—Cys—Ser—Met—Ileu—

Gly—Thr—Asn—Cys—Glu—Cys—Thr—Pro—Arg—Leu—

Ileu—Met—Glu—Gly—Leu—Ser—Phe—Ala—OH

The composition has a molecular weight of approximately 5274.

The gene which produces the AG1 toxin has been identified by employing a new procedure. The procedure uses a "polymerase chain reaction" (PCR) conducted under conditions which have recently been identified in the relevant literature. See, R. K. Saiki et al., *Science* 230, p. 1350 (1985); Saiki et al., "Primer-Directed Enzymatic Amplification of DNA with a Thermostable DNA Polymerase," *Science* 239, 487 (January 1988), which are collectively incorporated herein by this reference.

In order to clone the toxin gene two oligonucleotide primers were prepared. The first primer was specific only for the "poly A" tail of the mRNA. The second oligonucleotide primer was engineered from the cDNA of the coding gene sequence.

All of the mRNA in the RNA population was reverse transcribed to cDNA using the d(T) tailed primer. The specificity in the procedure comes with the amino terminal primer which is designed specifically from the protein sequence. Thus, only the cDNA which contains this sequence will be efficiently amplified in this system, as described in Saiki, et al.

Figure 2:
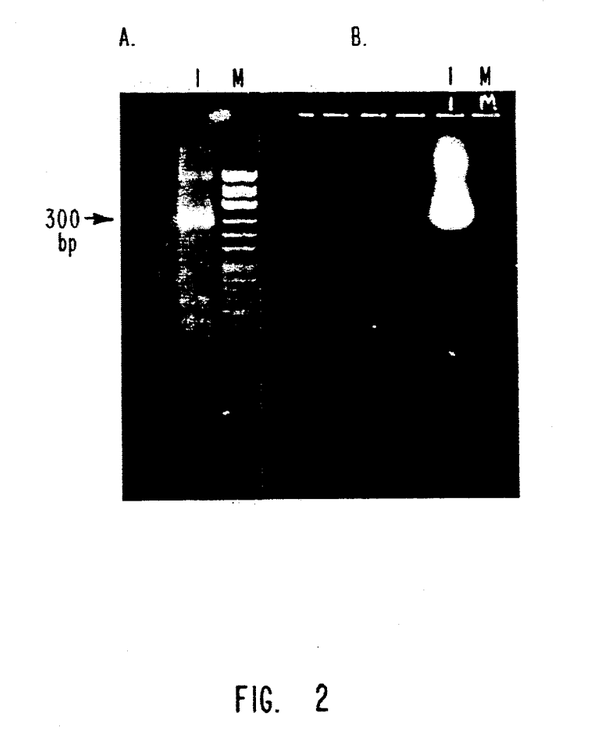
FIG. 2 is an autoradiograph of the southern analysis of the reaction products confirming the isolation and identification of the gene responsible for the production of AG1.

The analysis of the anchored PCR products obtained from the reverse transcribed Agelenopsis venom gland mRNA are shown in FIG. 2, as described in greater detail below. Southern hybridization with the internal probe confirmed the correct gene sequence. DNA sequencing of this anchored PCR product confirmed that it contained the complete coding sequence of AG1, as well as all DNA sequences preceding the poly (A) tail. The sequence of the gene is set forth in Table 4 below.

Analysis of the translated peptide sequence indicated a protein having a molecular weight of approximately 5,280 daltons, with 8 cysteine residues. This data is set forth below in Table 5. This data indicates that the gene sequence identified is that which is responsible for the production of AG1 in the *Agelenopsis aperta* spider.

Identification of the gene responsible for the production of AG1 facilitates the production of the toxin by using i.e., recombinant DNA techniques, and may result in the ability to genetically engineer higher plants with the ability to produce the toxin.

It has been found that AG1 produces blockade of synaptic transmission under certain conditions without affecting axonal conduction of action potentials. The AG1 toxin affects transmission of the nerve impulse across the synapse.

AG1 is also found to block transmission in certain central nervous system cells by blocking calcium currents. It is particularly noteworthy that AG1 is not acutely toxic to the cells tested and does not affect the electric excitability of the neurons themselves. Thus, this suggests that AG1's effects are not produced by acute cytotoxic action. Simply stated, CNS transmission is blocked without damaging the cells involved.

It is a primary object of the present invention to provide calcium channel blockers and methods for their use which have specific and identifiable effects on an organism.

Another object of the present invention is to provide a specific calcium channel blocker which affects the central nervous system.

It is another object of the present invention to provide calcium channel blockers for use as research tools and for use in the clinical setting.

It is also an object of the present invention to identify the amino acid sequence of the AG1 toxin responsible for blocking synaptic transmission in the central nervous system.

It is a similar object of the present invention to isolate and identify the gene responsible for production of the AG1 toxin that blocks synaptic transmission.

These and other objects of the present invention will become apparent upon reading the following detailed description and appended claims.

DETAILED DESCRIPTION OF THE PREFERRED EMBODIMENTS

As discussed above, the present invention is related to new and unique calcium channel blockers, methods for their isolation, and methods of application of such molecules. In particular, the present invention relates to the use of isolated toxins obtained from spider venom for use as specific calcium channel blockers.

It has been found within the scope of the present invention that certain spider venoms may selectively act on the central nervous system. More particularly, it has been found that spider venoms can have specific activities on calcium channels within the organism.

An additional benefit of the present invention is that the isolated toxins act without significant cytotoxicity. Thus, the toxins do not block channels by destroying the cells within the systems in which they are active. Additionally, the toxins of the present invention generally act without affecting axonal conduction within the nervous system. It will be appreciated, therefore, that only calcium channels are affected by the toxin that acts on the central nervous system.

I. Techniques for Isolation of Venoms

In order to avoid impurities within the spider venom and the isolated toxins, the spider venom which was used for the tests described below was electrically milked from the spiders using a method which employs safeguards to prevent contamination of the venom by abdominal regurgitate or hemolymph.

Once the spider venom is obtained by electrical milking techniques, it is further purified using gel filtration chromatography or other similar related techniques. In addition, it is frequently desirable for final fractionation of the spider venom to be performed by high performance liquid chromatography ("HPLC").

Thus, using the technique of electrically milking the spider coupled with gel filtration chromatography and high performance liquid chromatography it is possible to obtain purified and usable spider toxins. It will be appreciated, however, that other equivalent techniques may also be employed the spider toxins used.

II. Specific Toxin within the Scope of the Invention

While it will be appreciated that additional toxins may also fall within the scope of the present invention, the following relates to the identification and isolation of a specific toxin which has been found to have the characteristics required for a usable calcium channel blocker as described above. In addition, the native gene responsible for the production of the toxin has been identified.

Using the techniques described above relating to the collection of venom, a toxin has been isolated from the *Agelenopsis aperta* spider having a molecular weight of approximately 5274 and the peptide sequence described herein. It has been found that AG1 blocks synaptic transmission in in vitro preparations of chick cochlear nucleus and rat hippocampus.

In experiments performed using the toxin, it has been found that the toxin is very potent in that 100 nanomolar concentrations produce half-maximol blockade of synaptic transmission in rat hippocampus slices and 1 micromolar concentrations produce complete blockade.

Complete blockade using AG1 on central nervous system cells occurs in the absence of presynaptic action potentials and the time course of action is unaffected by the rate of presynaptic stimulation. Partial blocks achieved by brief exposure to dilute AG1 toxin were stable for at least one hour and were unaffected by increases or decreases in stimulation rate. Partial blockade by AG1, however, can be largely reversed by increasing the extracellular calcium concentration. Subsequent reduction in calcium concentration, however, causes the postsynaptic response to decline to its previous level of partial blockade.

In the absence of toxin, the same increase in calcium has no effect on the amplitude of responses. These results indicate that this toxin acts on calcium channels to produce long lasting blockade of transmission. The effects are independent of stimulation frequency, suggesting that the toxin does not act primarily on synthesis or reuptake of transmitter. Calcium antagonism of the effects makes it improbable that the toxin causes massive release of transmitter.

In summary, it is found that this toxin is antagonized by increasing calcium concentrations and produces blockade of synaptic transmission in cochlear chick nucleus and rat hippocampus without affecting axonal conduction. In addition, this toxin has been found not to be acutely toxic and does not affect the electrical excitability of cochlear nucleus neurons themselves, indicating that its effects are not produced by acute cytotoxic action.

III. Comparison with other Calcium Channel Blockers

Receptor- and voltage-activated calcium channels are of fundamental importance in the survival and function of virtually all cell types. Entry of calcium through such channels regulates a variety of cellular activities including contraction of cardiovascular muscle and the release of neurotransmitters from nerve cells. There are presently three major known classes of organic calcium channel blockers, as opposed to inorganic blockers such as manganese or lanthanum. These organic calcium channel blockers include: phenylalkylamines such as verapamil; benzothiazepines such as diltiazem; and dihydropyridines such as nifedipine.

The currently available organic calcium channel blockers have pronounced actions on heart and vascular smooth muscle, although relative selectivity for these two types of tissues varies among these compounds. A second notable feature of these agents is that, although they will bind to brain tissue, they have either no effect or a relatively minor effect on the function of neurons in the central nervous system, particularly as compared to their striking effects on heart and vascular smooth muscle.

The AG1 toxin derived from *Agelenopsis aperta* venom has properties that very clearly distinguish it from the currently available calcium channel blockers. AG1 acts primarily, if not exclusively, on neuronal calcium channels as opposed to heart or vascular smooth muscle calcium channels. This tissue selectivity is opposite to that seen in the compounds mentioned above.

Because of the importance of calcium and calcium channels to the function of neurons, there are a variety of potential applications of compounds within the scope of the present invention. Calcium influx through channels mediates neurotransmitter release and modulates neuronal excitability. Selective blockers of neuronal calcium channels, therefore, could modify neuronal excitability by effects on both presynaptic and postsynaptic calcium channels.

Accordingly, appropriate calcium channel blockers could be used in treatment of several neurological disorders that are thought to involve excessive neuronal excitation: e.g., stroke, traumatic head injury, epilepsy, and neurodegenerative disorders such as Huntington's disease and Alzheimer's disease.

IV. Amino Acid Sequencing

AG1 was further analyzed in order to determine its amino acid sequence. Initially, venom was obtained from *Agelenopsis aperta* spiders using the techniques described herein. Active fractions of the venom were pooled and subjected to separation by ion-exchange chromatography. The fraction of the venom constituting the AG1 toxin was then isolated using the techniques described herein, including in Example 2. The AG1 toxin was then analyzed by employing known techniques and with the aid of a mechanical amino acid analyzer.

The results of the amino acid sequence analyses of AG1 yielded a 48 amino acid peptide. The peptide has a molecular weight in the range of from approximately 5272 to approximately 5282 daltons. The sequence of the peptide as identified by the procedure set forth above is as follows:

Glu—Asp—Asn—Cys—Ileu—Ala—Glu—Asp—Tyr—Gly—Lys—

Cys—Thr—Trp—Gly—Gly—Thr—Lys—Cys—Cys—Arg—Gly—Arg—

Pro—Cys—Arg—Cys—Ser—Met—Ileu—Gly—Thr—Asn—Cys—

Glu—Cys—Thr—Pro—Arg—Leu—Ileu—Met—Glu—Gly—Leu—

Ser—Phe—Ala—R

V. Identification of the Gene Responsible for Production of AG1

Employing the amino acid sequence data obtained as described above, the gene responsible for the production of AG1 was isolated and identified.

Initially, the possible codons responsible for each amino acid in the sequenced peptide were identified and plotted. Table 1 lists the possible codons which relate to each amino acid in the peptide. It will be appreciated that the possible number of sequences available to produce the peptide is very large, due to the fact that some of the amino acids can be produced by up to six (6) different nucleotide sequences. When it is appreciated that a 48 amino acid peptide is involved, with most of the amino acids possibly being encoded by multiple nucleotide sequences, it will be appreciated that sequential testing using possible oligonucleotide probes was found to be impractical.

TABLE 1

AG1 IN ALL CODONS.

| Pos | AA | Codons |
|---|---|---|
| 1 | GLU | GAA, GAG |
| 2 | ASP | GAC, GAT |
| 3 | ASN | AAC, AAT |
| 4 | CYS | TGT, TGC |
| 5 | ILE | ATT, ATC, ATA |
| 6 | ALA | GCT, GCC, GCG, GCA |
| 7 | GLU | GAA, GAG |
| 8 | ASP | GAC, GAT |
| 9 | TYR | TAC, TAT |
| 10 | GLY | GGT, GGC, GGA, GGG |
| 11 | LYS | AAG, AAA |
| 12 | CYS | TGT, TGC |
| 13 | THR | ACT, ACC, ACA, ACG |
| 14 | TRP | TGG |
| 15 | GLY | GGT, GGC, GGA, GGG |
| 16 | THR | ACT, ACC, ACA, ACG |
| 17 | LYS | AAG, AAA |
| 18 | CYS | TGT, TGC |
| 19 | LYS | AAG, AAA |
| 20 | CYS | TGT, TGC |
| 21 | ARG | AGA, AGG, CGT, CGC, CGA, CGG |
| 22 | GLY | GGT, GGC, GGA, GGG |
| 23 | ARG | AGA, AGG, CGT, CGC, CGA, CGG |
| 24 | PRO | CCA, CCT, CCG, CCC |
| 25 | CYS | TGT, TGC |
| 26 | ARG | AGA, AGG, CGT, CGC, CGA, CGG |
| 27 | CYS | TGT, TGC |
| 28 | SER | TCT, TCC, TCA, TCG, AGT, AGC |
| 29 | MET | ATG |
| 30 | ILE | ATT, ATC, ATA |
| 31 | LYS | AAG, AAA |
| 32 | GLY | GGT, GGC, GGA, GGG |
| 33 | THR | ACT, ACC, ACA, ACG |
| 34 | ASN | AAC, AAT |
| 35 | CYS | TGT, TGC |
| 36 | GLU | GAA, GAG |
| 37 | GLY | GGT, GGC, GGA, GGG |
| 38 | CYS | TGT, TGC |
| 39 | THR | ACT, ACC, ACA, ACG |
| — | PRO | CCA, CCT, CCG, CCC, CGA, CGC |
| — | ARG | AGA, AGG, CGT, CGC, CTC |
| 40 | LEU | TTG, CTA, TTA, CTG, CTT |
| 41 | ILE | ATT, ATC, ATA |
| 42 | MET | ATG |
| 43 | GLU | GAA, GAG |
| 44 | GLY | GGT, GGC, GGA, GGG |
| 45 | LEU | TTG, CTA, TTA, CTG, CTT, CTC |
| 46 | SER | TCT, TCC, TCA, TCG, AGT, AGC |
| 47 | PHE | TTC, TTT |
| 48 | ALA | GCT, GCC, GCG, GCA |
| 50 | | |
| 55 | | |
| 60 | | |

Figure 1:
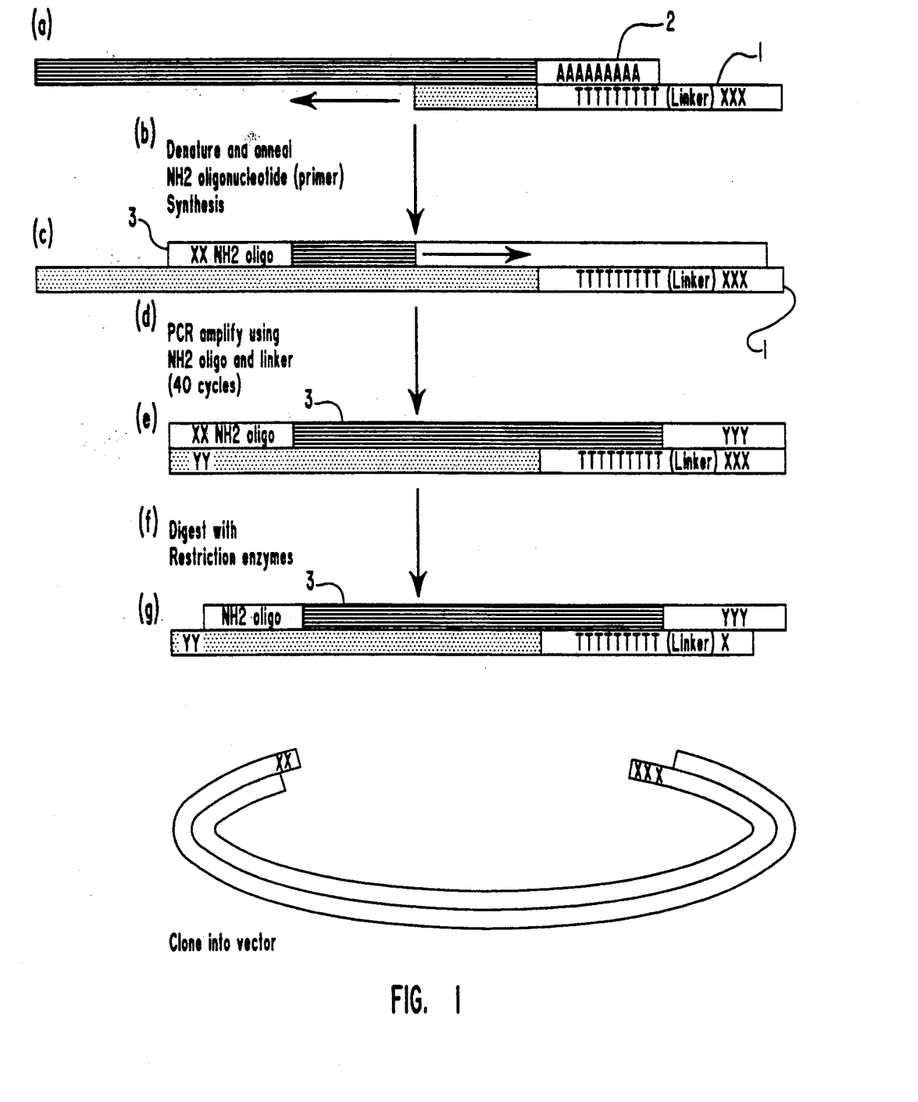
FIG. 1 is a schematic drawing representing the procedure employed in identifying and isolating the gene responsible for the production of AG1.

Accordingly, a technique employing PCR was developed and is illustrated schematically in FIG. 1. PCR is well documented in the literature, including the citations set forth above. Essentially PCR allows the production of a selected DNA sequence when the two terminal portions of the sequence are known. Primers, or oligonucleotide probes, are obtained which correspond to each end of the sequence of interest. Using PCR, the central portion of the DNA sequence is then synthetically produced.

In sequencing the gene corresponding to AG1, a first primer was selected which corresponds to the poly (A) terminus, also sometimes referred to herein as a d(T) tailed primer. The d(T) tailed primer also includes a restriction site downstream from the d(T) segment. In this particular procedure a NotI restriction site was included (CGCGGCCGC). The d(T) tailed primer is illustrated at 1 in step (a) of FIG. 1, and the mRNA of the spider is illustrated at 2. An mRNA is then reverse transcribed to cDNA using the d(T) tailed primer as is represented graphically by the arrow in step (a).

The synthetic cDNA is then denatured and annealed as is shown in step (b). At this point an appropriate NH2 primer or oligonucleotide is synthesized. See, Table 2. In the synthesis of the primer the data of Table 1 is employed to determine the possible sequences which may be usable. In addition, in order to select the sequences which are most likely to result in the actual sequence, preference data of the type illustrated in Table 3 is employed.

At this point, the primer 3 is bound to the denatured cDNA and a cDNA sequence is produced as illustrated at step (c) in FIG. 1 Because the primer is specific to the desired mRNA sequence, only the cDNA which corresponds to the chosen sequence will be effectively amplified.

The resulting material is amplified over multiple cycles, as is taught in PCR procedure as is shown at step (d). In this particular case amplification took place over 39 cycles in order to assure maximum amplification.

The result of the process is a synthetic cDNA sequence which corresponds to that of the gene of interest. This is illustrated at (e). The DNA produced is then digested with the appropriate restriction enzymes and cleaved at the engineered restriction site. (Cleaving the restriction site enables it to be cloned). This step is illustrated at (f).

TABLE 2

Primers for PCR amplification of AG1 Gene Sequnces

| | AA #: | | | | | | | |
|---|---|---|---|---|---|---|---|---|
| | 1 | 2 | 3 | 4 | 5 | 6 | 7 | 8 |
| Amino acid: | E | D | N | C | I | A | E | D |
| All possible codons: | GAG | GAC | AAC | TGT | ATT | GCA | GAG | GA |
| | GAA | GAT | AAT | TGC | ATC | GCC | GAA | |
| | | | | | ATA | GCG | | |
| | | | | | | GCT | | |
| NH—K Oligo: | GAG | GAC | AAC | TGC | ATT | GCA | GAG | GA |
| | | GAT | AAT | | ATC | GCC | GAA | |
| | | | | | | GCG | | |
| | | | | | | GCT | | |

TABLE 3

| | | | Drosophila Preference (1) | | |
|---|---|---|---|---|---|
| A.A. | # of codons | Favored codons | h = high bias gene | l = low bias gene | Human Preference(2) |
| C | 2 | UGC | h = 0.97 | l = 0.65 | 0.70 |
| D | 2 | GAC | h = 0.61 | l = 0.22 | 0.62 |
| E | 2 | GAG | h = 0.91 | l = 0.64 | 0.60 |
| F | 2 | UUC | h = 0.94 | l = 0.57 | 0.65 |
| H | 2 | CAC | h = 0.86 | l = 0.57 | 0.58 |
| K | 2 | AAG | h = 0.97 | l = 0.60 | 0.55 |
| N | 2 | AAC | h = 0.94 | l = 0.44 | 0.66 |
| Q | 2 | CAG | h = 0.99 | l = 0.56 | 0.74 |
| Y | 2 | UAC | h = 0.89 | l = 0.52 | 0.53 |
| I | 2 | AUC | h = 0.75 | l = 0.32 | 0.64 |
| | | AUU | h = 1.00 | l = 0.74 | 0.87 |
| A | 4 | GCC | h = 0.94 | l = 0.71 | 0.71 |
| | | GCU | | | |
| G | 4 | GGC | h = 0.75 | l = 0.64 | 0.59 |
| | | GGU | | | |
| P | 4 | CCC | h = 0.84 | l = 0.52 | 0.65 |
| | | CCA | | | |
| T | 4 | ACC | h = 0.76 | l = 0.40 | 0.47 |
| | | ACG | h = 0.81 | l = 0.63 | 0.59 |
| V | 4 | GUC | h = 0.85 | l = 0.68 | 0.77 |
| | | GUG | | | |
| L | 6 | CUG | h = 0.71 | l = 0.34 | 0.46 |
| | | CUC | h = 0.83 | l = 0.49 | 0.68 |
| R | 6 | CGC | h = 0.95 | l = 0.37 | 0.28 |
| | | CGU | | | |
| S | 6 | UCC | h = 0.65 | l = 0.45 | 0.33 |
| | | UCG | | | |
| | | AGC | h = 0.84 | l = 0.62 | 0.62 |

(1)Sharp, P. et al., Nucl. Acids Res. 16, 8207 (1988).
(2)Lathe, R. J. Mol. Biol. 183, 1 (1985).

Finally, the produced cDNA sequence can be cloned into an appropriate vector using conventional techniques, analyzed and sequenced. The DNA sequence is presented in Table 4. A direct amino acid translation of this anchored PCR product revealed that it corresponded to the complete coding sequence for AG1, as well as all DNA sequences preceding the poly (A) tail. See, Table 5. The exact function and purpose of the 5 portion of the gene between the stop codon for the peptide and the beginning of the poly (A) tail is not known at this time.

The complete sequence is set forth in Table 4. Table 4 shows the DNA sequence above the corresponding peptide for each of the 48 peptides. Table 4 also sets forth the DNA sequence between the end of the material useful for encoding the peptide and the beginning of the poly (A) tail, as well as the tail itself. Additional detail concerning the procedure described above is included herein in Example 3.

FIG. 2 illustrates the results of Southern analysis of one-tenth of the reaction products. "A" is an autoradiograph of an ethidium stained gel of one-tenth of the reaction products obtained from the amplification of 25 ng mRNA using the amino primer d(T) tailed primer adapter. The size marker lane was Hinf I digested φ174 DNA. "B" is the results of Southern analysis of the reaction products confirmed by probing with an internal gene sequence. The results show dramatically the effectiveness of the technique described above.

TABLE 5 peptideK AA Composition Data
Calculated Molecular Weight = 5280.729
Estimated pI = 6.465
Amio Acid Composition:

|  | Number | Percent |
|---|---|---|
| Non-polar: | | |
| Ala | 2 | 4.17 |
| Val | 0 | 0.00 |
| Leu | 2 | 4.17 |
| Ile | 3 | 6.25 |
| Pro | 2 | 4.17 |
| Met | 2 | 4.17 |
| Phe | 1 | 2.08 |
| Trp | 1 | 2.08 |
| Polar: | | |
| Gly | 6 | 12.50 |
| Ser | 2 | 4.17 |
| Thr | 4 | 8.33 |
| Cys | 8 | 16.67 |
| Tyr | 1 | 2.08 |
| Asn | 2 | 4.17 |
| Gln | 0 | 0.00 |
| Acidic: | | |
| Asp | 2 | 4.17 |
| Glu | 4 | 8.33 |
| Basic: | | |
| Lys | 2 | 4.17 |
| Arg | 4 | 8.33 |
| Bis | 0 | 0.00 |

Recombinant Expression

Provision of a suitable DNA sequence encoding the desired protein permits the production of the protein

TABLE 4

Translated Sequence
Sequence Range: 1 to 317

```
          10              20              30              40              50
           •               •               •               •               •
GAC GAT AAT TGC ATT GCG GAG GAT TAC GGA AAA TGC ACA TGG GGC GGA ACA
CTC CTA TTA ACG TAA CGC CTC CTA ATG CCT TTT ACG TGT ACC CCG CCT TGT
Glu Asp Asn Cys Ile Ala Glu Asp Tyr Gly Lys Cys Thr Trp Gly Gly Ghr 60              70              80              90              100
           •               •               •               •               •
AAA TGC TGC CCG GGA CGC CCA TGT CGC TGC AGC ATG ATT GGG ACG AAT TGT
TTT ACG ACG GCC CCT GCG GGT ACA GCG ACG TCG TAC TAA CCC TGC TTA ACA
Lys Cys Cys Arg Gly Arg Pro Cys Arg Cys Ser Met Ile Gly Thr Asn Cys 110             120             130             140             150
           •               •               •               •               •
GAA TGT ACA CCA AGA TTA ATA ATG GAA GGT TTG TCA TTT GCG TGA ACT TGG
CTT ACA TGT GGT TCT AAT TAT TAC CTT CCA AAC AGT AAA CGC ACT TGA ACC
Glu Cys Thr Pro Arg Leu Ile Met Glu Gly Leu Ser Phe Ala End 160             170             180             190             200
           •               •               •               •               •
TAA AGA TCT CAA GCA GAA TAG CGA TGG AGC AGA ACA TCT AGT TTA CTT ACA
ATT TCT AGA GTT CGT CTT ATC GCT ACC TCG TCT TGT AGA TCA AAT GAA TGT 210             220             230             240             250
           •               •               •               •               •
ATT ATA TTA ATA TTA TAT TAA ATA ATC CTC AAA TAA GGA TGT ATA ATT TTG
TAA TAT AAT TAT AAT ATA ATT TAT TAG GAG TTT ATT CCT ACA TAT TAA AAC 260             270             280             290             300
           •               •               •               •               •
TGA TGA AAT TAA AAA TTC TTT ATT CGC AAA AAA AAA AAA AAA AAA AAA AAA
ACT ACT TTA ATT TTT AAG AAA TAA GCG TTT TTT TTT TTT TTT TTT TTT TTT

310
           •
AAA AAA AAA AA
TTT TTT TTT TT
``` using recombinant techniques now well known in the art. The coding sequence can be obtained by retrieving a cDNA or genomic sequence from a native source of the protein or can be prepared synthetically using the accurate amino acid sequence from the nucleotide sequence of the gene. When the coding DNA is prepared synthetically, advantage can be taken of known codon preferences of the intended host.

Expression systems containing the requisite control sequences, such as, promoters, and preferably enhancers and termination controls, are readily available and known in the art for a variety of hosts.

Thus, the desired proteins can be prepared in both procaryotic and eucaryotic systems, resulting, in the case of many proteins, in a spectrum of processed forms. The most commonly used procaryotic system remains E. coli, although other systems such as B. subtillis and Pseudomonas could also be used. Suitable control sequences for procaryotic systems include both constitutive and inducible promoters including the lac promoter, the trp promoter, hybrid promoters such as tac promoter, and the lambda phage $P_1$ promoter. In general, foreign proteins may be produced in these hosts either as fusion or mature proteins; when the desired sequences are produced as mature proteins, the sequence produced may be preceded by a methionine which is not necessarily efficiently removed. Accordingly, the peptides and proteins claimed herein may be preceded by an N-terminal Met when produced in bacteria. Moreover, constructs may be made wherein the coding sequence for the peptide is preceded by an operable signal peptide which results in the secretion of the protein. When produced in procaryotic hosts in this matter, the signal sequence is removed upon secretion.

A wide variety of eucaryotic hosts is also now available for production of recombinant foreign proteins. As in bacteria, eucaryotic hosts may be transformed with expression systems which produce the desired protein directly, but more commonly signal sequences are provided to effect the secretion of the protein. Eucaryotic systems have the additional advantage that they are able to process introns which may occur in the genomic sequences encoding proteins of higher organisms. Eucaryotic systems also provide a variety of processing mechanisms which result in, for example, glycosylation, oxidation or derivatization of certain amino acid residues, conformational control, and so forth.

Commonly used eucaryotic systems include yeast, insect cells, mammalian cells, avian cells, and cells of higher plants. The list is not exhaustive. Suitable promoters are available which are compatible and operable for use in each of these host types as well as are termination sequences and enhancers. As above, promoters can be either constitutive or inducible. For example, in mammalian systems, the MTII promoter can be induced by the addition of heavy metal ions.

The particulars for the construction of expression systems suitable for desired hosts are well known to those in the art. For recombinant production of the protein, the DNA encoding it is suitably ligated into the expression system of choice, and the system is then transformed into the compatible host which is then cultured and maintained under conditions wherein expression of the included gene takes place. The protein thus produced is recovered from the culture, either by lysing the cells or from the culture medium as appropriate.

A "mutation" in a protein alters its primary structure (relative to the commonly occurring or specifically described protein) due to changes in the nucleotide sequence of the DNA which encodes it. These mutations specifically include allelic variants. Mutational changes in the primary structure of a protein result from deletions, additions, or substitutions. Such changes involving only 3 or less amino acid residues are generally preferred. A "deletion" is defined as a polypeptide in which one or more internal amino acid residues are absent. An "addition" is defined as a polypeptide which has one or more additional internal amino acid residues as compared to the wild type. A "substitution" results from the replacement of one or more amino acid residues by other residues. A protein "fragment" is a polypeptide consisting of a primary amino acid sequence which is identical to a portion of the primary sequence of the protein to which the polypeptide is related.

Preferred "substitutions" are those which are conservative, i.e., wherein a residue is replaced by another of the same general type. As is well understood, naturally-occurring amino acids can be subclassified as acidic, basic, neutral and polar, or neutral and nonpolar. Furthermore, three of the encoded amino acids are aromatic. It is generally preferred that encoded peptides differing from the native form contain substituted codons for amino acids which are from the same group as that of the amino acid replaced.

Thus, in general, the basic amino acid Lys, Arg, and His are interchangeable; the acidic amino acids aspartic and glutamic are interchangeable; the neutral polar amino acids Ser, Thr, Cys, Gln, and Asn are interchangeable; the nonpolar aliphatic acids Gly, Ala, Val, Ils, and Leu are conservative with respect to each other (but because of size, Gly and Ala are more closely related and Val, Ile and Leu are more closely related), and the aromatic amino acids Phs, Trp, and Tyr are interchangeable.

While proline is a nonpolar neutral amino acid, it represents difficulties because of its effects on conformation, and substitutions by or for proline are not preferred, except when the same or similar conformational results can be obtained. Polar amino acids which represent conservative changes include Ser, Thr, Gln, Asn; and to a lesser extent, Met. In addition, although classified in different categories, Ala, Gly, and Ser seem to be interchangeable, and Cys additionally fits into this group, or may be classified with the polar neutral amino acids. Some substitutions by codons for amino acids from different classes may also be useful.

Because recombinant materials for the proteins of the invention are provided, these proteins can be made recombinantly. Because of the variety of post-translational characteristics conferred by various host cells, various modifications for the naturally-occurring proteins will also be obtained. A "modified" protein differs from the commonly occurring protein as a result of post-translational events which change the glycosylation or lapidation pattern, or the primary, secondary, or tertiary structure of the protein.

It should be further noted that if the proteins herein, such as AG1, are made synthetically, substitutions by amino acids which are not encoded by the gene may also be made. Alternative residues include, for example, the ωamino acids of the formula $H_2N(CH_2)_nCOOH$ wherein n is 2-6. These are neutral, nonpolar amino acids, as are sarcosine (Sar), t-butylalanine (t-BuA), t-butylglycine (t-BuG), N-methyl Ila (N-MeIle), and norleucine (Nle). Phenylglycine, for example, can substituted for Trp, Tyr or Phe an aromatic neutral amino acid; citrulline (Cit) and methionine sulfoxide (MSO) are polar but neutral, cyclohexyl alanine (Cha) is neutral and nonpolar, cysteic acid (Cya) is acidic, and ornithine (Orn) is basic. The conformation conferring properties of the proline residues may be obtained if one or more of these is substituted by hydroxyproline (Hyp).

V. EXAMPLES

The following examples are given to illustrate particular compositions and methods within the scope of the present invention but they are not intended to limit the scope of the present invention.

EXAMPLE 1

A spider toxin within the scope of the present invention was isolated from the *Agelenopsis aperta* spider. Spider venom was obtained from, and species identification provided by, Spider Pharm, Inc. of Black Canyon City, Ariz. and Natural Product Sciences, Inc., Salt Lake City, Utah. *Agelenopsis aperta* spiders were electrically milked using a method that employs safeguards to prevent contamination of venom by abdominal regurgitate or hemolymph. Venom was diluted 1 to 10 with avian Tyrode solution (140 mM NaCl, 4 mM KCl, 4 mM NaHCO$_3$, 1 mM MgSO$_4$, 3 mM CaCl, 1.2 mM NaH$_2$PO$_4$, 10 mM HEPES, 10 mM glucose) and fractionated by gel filtration using Bio-Gel P-10 and a 0.7×30 cm column and collected in 0.5 ml fractions. These fractions were assayed for blockade of synaptic below.

HPLC separation of active gel filtration fractions was performed using a Vydac C-18 reverse phase column. Components were eluted from the column over a period of 60 minutes using a 0–60% linear gradient of 60% acetonitrile in 0.1% trifluoroacetic acid. Elution was monitored by absorbance detection at 214 nm. Peaks were collected manually, dried down, stored at −20° C., and then reconstituted with avian Tyrode before use.

For gel electrophoresis, a 15 ul sample of each gel filtration fraction was mixed with 7.5 ul of 3X sample buffer (18% 1M tris-HCL, pH 6.8, 15% 2 mercaptoethanol, 30% glycerol, 7% sodium dodecyl-sulfate, 0.001% bromphenol blue) and the entire sample was loaded onto a 10% to 20% gradient polyacrylamide gel using the slab method. Electrophoresis was performed at 20 watts constant power for three hours. Gels were stained with Coomassie blue.

The toxin so isolated had a molecular weight of approximately 6,000 as estimated from SDS polyacrylamide gels as was designated AG1. The toxin was bath-applied to cochlear nucleus neurons in an in vitro preparation of chick brain stem. Upon stimulation of the cochlear nerve innervating the cochlear nucleus, it was found that the toxin blocked transmission between the cochlear nerve afferents and the cochlear nucleus neurons.

EXAMPLE 2

*Agelenopsis aperta* spiders were electrically milked using a method that employs safeguards to prevent contamination of venom by abdominal regurgitate or hemolymph. Venom was diluted to 1 to 10 with avian Tyrode solution and fractionated by gel filtration using Bio-Gel P-10 and a 0.7×30 cm column and collected in 0.5 ml fractions. These fractions were assayed for blockage of synaptic transmission using an in vitro preparation of the chick cochlear nucleus. Active fractions (fractions 7-9) were pooled and subjected to separation by ion-exchange chromatography using NaCl concentrations of 10–300 mM, 0.5 ml fractions were again collected and assayed. A fraction eluting in 70 mM NaCl contained the material active in blocking synaptic transmission in the chick cochlear nucleus. This fraction was then subjected to separation by high-performance liquid chromatography (HPLC) using a Vydac C-18 reverse-phase column. Components were eluted from the column over a period of 60 minutes using a 0–60% linear gradient of 60% acetonitrile in 0.1% trifluorooacetic acid. Elution was monitored by absorbance detection at 214 nm. Peaks were collected manually, dried down, stored at −20° C. and then reconstituted in avian Tyrode solution before being re-assayed on the chick cochlear nucleus preparation. A single major peak in the chromatogram appeared to contain most of the activity in the AG1 fraction; this peak was subjected to amino acid composition and sequence analyses using the following methods.

Samples of AG1 were subjected to amino acid analysis by known techniques. The samples were hydrolyzed in vacuo with 6N HCL, at 105° C. for 24 hours. Acid was removed by drying in a Speed-Vac and the residue was analyzed by ion-exchange chromatography on a Beckman Model 121 amino acid analyzer. Other samples of AG1 were reduced, carboxymethylated, and analyzed in a Beckman 890D spinning cup peptide sequencer using a 0.1M Quadrol program. Polybrene carrier was precycled by running four steps in the presence of 100 nmol of Ser-Gly. PTH-amino acids were analyzed by HPLC using methods described by Gray et al. (*J. Biol. Chem.* 256:4734–4740, 1981).

The results of amino acid and sequence analyses of AG1 yielded the following 48-amino acid peptide:

Glu—Asp—Asn—Cys—Ileu—Ala—Glu—Asp—Tyr—Gly—Lys—

Cys—Thr—Trp—Gly—Gly—Thr—Lys—Cys—Cys—Arg—Gly—Arg—

Pro—Cys—Arg—Cys—Ser—Met—Ileu—Gly—Thr—Asn—Cys—

Glu—Cys—Thr—Pro—Arg—Leu—Ileu—Met—Glu—Gly—Leu—

Ser—Phe—Ala—OH

EXAMPLE 3

The coding gene for AG1 from Agelenopsis was isolated. The procedure for isolating the gene is outlined as follows:
1. Isolate RNA from spider; purify mRNA.
2. Synthesize oligonucleotide primer corresponding to the amino-terminal protein sequence data and internal primer if data available.
3. Reverse transcribe the RNA using a d(T) primer carrying an engineered restriction site.
4. PCR amplify the coding sequence and any downstream sequences preceding the poly (A) tail using amino-specific and d(T) primers.
5. Analyze PCR amplified products (verify with internal probe if available). Isolate product.
6. Digest with appropriate enzymes, clone and sequence.

Step #1:

Spiders were collected and identified at Natural Product Sciences, Inc., Salt Lake City, Utah as *Agele-* nopsis aperta. Venom glands were pulled from anesthetized spiders and quickly frozen in liquid nitrogen. RNA was extracted from the venom glands using the protocol of Chomczynski and Sacchi (Analytical Biochemistry 162, 156 (1987)). Polyadenylated messenger RNA (nRNA) was purified using oligo d(T) cellulose (Pharmacia LKB, Sweden) chromatography.

Step #2:

An oligonucleotide corresponding to residues 1 through 8 of the peptide K amino acid sequence was designed using some Drosophila codon preferences to reduce degeneracy. The cDNA synthesis (antisense) primer was composed of a run of 15 deoxythymidine residues adjacent to a Not I restriction enzyme site. An internal oligonucleotide probe was synthesized to represent amino acid sequence 10 to 16 with all possible preferences. The sense primer and internal primer were synthesized at the University of Utah, Howard Hughes Medical Institute contract facility. The d(T) Not I primer was purchased from Promega (Madison, Wis.).

Step #3: cDNA synthesis

Messenger RNA was reverse transcribed to cDNA with murine leukemia virus reverse transcriptase (Bethesda Research Laboratories, Maryland) using the manufacturer's protocol. The 20 ul reaction mixture contained the enzyme buffer as supplied in a cDNA synthesis kit (Boehringer Mannheim, Indiana), 50 ng of mRNA, 2 units of RNase H, 30 ng of d(T)Not I primer, 1 mM each deoxynucleoside triphosphates, and 100 u of reverse transcriptase. The reaction mixture was incubated for 1 h at 37° C. and continued for 10 minutes at 42° C. The reaction mixture was ethanol precipitated and resuspended in 20 ul $H_2O$.

Step #4: Amplification

Primer directed enzymatic amplification of DNA with a thermostable DNA polymerase was initially described by Saiki, et. al. (Science, 239:487 (1988)). For our application, 10 ul of the venom gland cDNA was used as template in a polymerase chain reaction containing reagents contained in the GeneAmp ™ DNA amplification kit (Perkin Elmer Cetus, California). The amplification reaction contained the sense and antisense primers in a 2 uM concentration, 100 uM of each deoxynucleotide triphosphate, and 4 units of the thermostable recombinant Taq polymerase. The reaction was run in a programmable heat block manufactured by Coy Laboratories (Ann Arbor, Mich.). It was started by denaturing the RNA-cDNA hybrid at 95° C. for 2 minutes, annealing the primers for 2 minutes at 37° C., and then extending the primers at 72° C. for 1 minute. This cycle was repeated twice and the program then switched to an identical profile incorporating an elevated annealing temperature of 54° C. This cycle was repeated 35 times. After the final cycle, the samples were chilled at 5° C.

Step #5:

One-tenth of the reaction mixture was run on a composite gel containing 3% NuSieve/1% SeaKem agaroses (FMC, Rockland, Me.) in Tris/borate/EDTA (TBE) buffer in the presence of ethidium bromide The gel was photographed and transferred onto Biotrace ™ nylon membrane (Gelman Sciences, Ann Arbor, Mich.) using an alkaline transfer protocol (E. M. Southern, J Mol Biol 98:503 (1975) and Reed and Mann, NAR 13:7277 (1985)). The membrane was prehybridized for 12 h at 42° C. in 5X SSC (0.75M NaCl/0.075M sodium citrate pH 7.0,) 20 mM sodium phosphate, pH 6.7, 2X Denhardt's (Sigma), and 0.1 mg/ml E. Coli tRNA (Boehringer Mannheim). To the buffer was then added $2 \times 10^5$ cpm/ml of 5' end $^{32}p$ labeled internal probe. Hybridization was continued at 42° C. for 24 h, and washing was done at 56° C. with 5X SSC/. The blot was autoradiographed using Kodak XAR film at $-70°$ C. for 1 hour.

Step #6:

The anchored PCR product visualized in FIG. 2 was purified through a Centricon-100 (Amicon) to remove unincorporated primers. The insert was then digested with the restriction enzyme Not I (MBR, Milwaukee, Wis.), utilizing the restriction site contained in the downstream primer. The vector, pKS (Statagene, LaJolla, Calif.), was double digested with EcoR V (U.S. Biochemical) and Not I to generate sites specific for directional cloning. Vector and insert were ligated and transformed into competent E. ^'i strain DH5α. Colony lifts were screened with the $^{32}P$ labeled internal probe and candidate colonies were further characterized by sequencing (U.S. Biochemical's Sequenase Version 2.0) mini-prep DNA using the internal probe as primer.

The inserts of three gene-containing candidates were then sequenced in entirety using commercially available external primers The sequence of one of the clones, pKS-KK, is presented in Table 4. The entire coding sequence as well as the 135 bp region preceding the poly (A) tail account for 282 base pairs of the sequence for the AG1 gene. Analysis of the translated peptide sequence suggested a protein of MW 5,280.73 daltons with 8 cysteine residues as shown in Table 5. If the cysteines are involved in disulfide bridges this suggests a molecular weight of 5,272.73 daltons which is in agreement with the mass spectroscopy data.

EXAMPLE 4

The high molecular weight Agelenopsis aperta toxin described in Example 1 was obtained using the same procedure as described in Example 1. Gel-filtration fractions having the effects described in Example 1 were diluted 1:150 with Tyrode and bath-applied for one minute to an in vitro preparation of the chick brain stem. This brief exposure to dilute toxin produced partial (about 50%) blockade of transmission.

These partial blocks were stable for at least one hour and were unaffected by increases or decreases in the rate of cochlear nerve stimulation over a range of 0-30 Hz. Partial blockade, however, was largely reversed by increasing extracellular calcium from 3 to 9 mM. Subsequent reduction of extracellular calcium back to 3 mM caused the postsynaptic response to revert to its previous level of partial blockade.

The result so obtained indicates that this toxin acts to produce long-lasting blockade of transmission. The finding that the effects of this toxin are independent of stimulation frequency suggests that the toxin does not act primarily on synthesis or reuptake of transmitter. The inverse relationship between extracellular calcium concentration and the blocking effects of the toxin indicates that the toxin likely acts on calcium channels. This action could be exerted on presynaptic calcium channels necessary for the release of transmitter and/or on postsynaptic calcium channels involved in the response of the cochlear nucleus neurons to synaptic stimulation.

EXAMPLE 5

The toxin AG1 described in Examples 1 through 4 is obtained in the manner described above from *Agelenopsis aperta* spider venom.

The toxin so obtained is applied and a complete blockade of synaptic transmission is achieved as described in Example 1. EAA agonists quisqualic acid and kainic acid are then individually bath-applied to the cochlear nucleus neurons at concentrations of 5 mM and 50 uM, respectively.

Application of these agonists at such concentrations normally reduces the ability of cochlear nucleus neurons to respond to direct electrical stimulation, presumably by depolarizing them by an action on EAA receptors. When applied in the presence of AG1 toxin the same effect is seen; that is, after 10 minutes of application of either quisqualic of kainic acids in the presence of AG1 toxin the response of cochlear nucleus neurons to direct antidromic stimulation is reduced by about 75%. The degree and time-course of this effect are not significantly different from those observed when either quisqualic of kainic acid is applied in the absence of AG1 toxin.

The result so obtained indicates that this toxin does not exert its blocking effects on synaptic transmission by a direct action on EAA receptors on the postsynaptic neuron but rather by a direct action of the toxin on calcium channels as suggested in Examples 1 and 3. If it were acting directly on EAA receptors it would be expected that the toxin would also block the effects of directly applied EAA agonists, such as quisqualic or kainic acid. The obtained result runs counter to that expectation.

EXAMPLE 6

The high molecular weight toxin described in Examples 1 through 5 (AG1) is obtained in the manner described above from *Agelenopsis aperta* spider venom.

The toxin so obtained is applied for the purpose of labeling calcium channels in neurons or other cell types. A radioactive label (such as $^{125}I$) is incorporated in the toxin molecule. Binding of the labeled toxin is then assayed using autoradiography of tissue sections or quantification (using scintillation counting) of binding to various tissue extracts such as synaptosomal or membrane preparations. Autoradiography of brain tissue sections labeled with the radioactive toxin reveals the regional distribution of the calcium channels to which the toxin binds. (A similar result is obtained by observing the binding pattern of the toxin conjugated to a fluorescent label.) The binding of the toxins to tissue extracts under various conditions, such as the presence of other drugs, provides information regarding the pharmacology of the calcium channel to which the toxin binds.

EXAMPLE 7

The AG1 toxin described in Examples 1-6 above is obtained in the manner described above from *Agelenopsis aperta* spider venom.

The toxin so obtained is tested for its ability to block synaptic transmission in an in vitro brain slice preparation of the rat hippocampus following generally the procedures described by Mueller et al. ("Noradrenergic responses in rat hippocampus: Evidence for mediation by alpha and beta receptors in the in vitro slice." Brain Research 214:113-126, 1981). When dissolved in the artificial cerebral spinal fluid bathing the hippocampal slice, the toxin shows a concentration-dependent ability (over the range from 1 nM to 1 $\mu$M) to inhibit the population spike (PS) recorded extracellularly from the CA1 region of the hippocampus with microelectrodes. In repeated experiments, the toxin is shown to produce half-maximal inhibition of the PS at a concentration of approximately 100 nanomolar. At concentrations that completely inhibit the PS, this toxin has no effect on axonal conduction, as reflected in the unchanged "afferent volley" component of the measured response. The magnitude of the PS suppression produced by this toxin is reduced as extracellular calcium concentration is increased from 2.4 mM (control) to 7.5 mM and 10 mM.

IV. SUMMARY

It will be appreciated that the present invention provides the ability to effectively block specific channels using the toxin. Similarly, specific channel blockers with activity on the central nervous system may have the potential to treat various neurological disorders. It has been found, for example, that these channel blockers may act as a treatment of epilepsy. In addition, channel blockers of the type disclosed in the present invention may also be used in treatments of stroke, traumatic head injury, and degenerative central nervous system diseases such as Huntington's disease.

In summary, it can be seen that the methods and compositions of the above invention accomplish the objectives set forth above. In particular, the present invention provides calcium channel blockers which can be used as research tools or in a clinical setting. In particular, the spider toxins of the present invention can be used as calcium channel blockers in the central nervous system.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A substantially pure peptide functioning as a calcium channel blocker and comprising the following amino acid sequence:

Glu—Asp—Asn—Cys—Ileu—Ala—Glu—Asp—Tyr—Gly—Lys—
Cys—Thr—Trp—Gly—Gly—Thr—Lys—Cys—Cys—Arg—Gly—
Arg—Pro—Cys—Arg—Cys—Ser—Met—Ileu—Gly—Thr—Asn—
Cys—Glu—Cys—Thr—Pro—Arg—Leu—Ileu—Met—Glu—Gly—
Leu—Ser—Phe—Ala and the pharmaceutically-acceptable salts thereof.

2. A substantially pure peptide as defined in claim 1 comprising the following amino acid sequence:

Glu—Asp—Asn—Cys—Ileu—Ala—Glu—Asp—Tyr—Gly—Lys—

Cys—Thr—Trp—Gly—Gly—Thr—Lys—Cys—Cys—Arg—Gly—

Arg—Pro—Cys—Arg—Cys—Ser—Met—Ileu—Gly—Thr—Asn—

Cys—Glu—Cys—Thr—Pro—Arg—Leu—Ileu—Met—Glu—Gly—

Leu—Ser—Phe—Ala—OH.

3. A substantially pure peptide as defined in claim 1 wherein the peptide has a calculated molecular weight of about 5274.

4. A substantially pure compound comprising the following amino acid sequence:

Glu—Asp—Asn—Cys—Ileu—Ala—Glu—Asp—Tyr—Gly—Lys—

Cys—Thr—Trp—Gly—Gly—Thr—Lys—Cys—Cys—Arg—Gly—Arg—

Pro—Cys—Arg—Cys—Ser—Met—Ileu—Gly—Thr—Asn—Cys—

Glu—Cys—Thr—Pro—Arg—Leu—Ileu—Met—Glu—Gly—Leu—

Ser—Phe—Ala.

5. A peptide isolated from the venom of the *Agelenopsis aperta* spider and comprising the following amino acid sequence:

Glu—Asp—Asn—Cys—Ileu—Ala—Glu—Asp—Tyr—Gly—Lys—

Cys—Thr—Trp—Gly—Gly—Thr—Lys—Cys—Cys—Arg—Gly—Arg—

Pro—Cys—Arg—Cys—Ser—Met—Ileu—Gly—Thr—Asn—Cys—

Glu—Cys—Thr—Pro—Arg—Leu—Ileu—Met—Glu—Gly—Leu—

Ser—Phe—Ala.

6. A peptide AG1 toxin responsible for producing blockade of synaptic transmission in the vertebrate central nervous system and having the amino acid sequence:

Glu—Asp—Asn—Cys—Ileu—Ala—Glu—Asp—Tyr—Gly—Lys—
Cys—Thr—Trp—Gly—Gly—Thr—Lys—Cys—Cys—Arg—Gly—Arg—
Pro—Cys—Arg—Cys—Ser—Met—Ileu—Gly—Thr—Asn—Cys—
Glu—Cys—Thr—Pro—Arg—Leu—Ileu—Met—Glu—Gly—Leu—
Ser—Phe—Ala in purified and isolated form.

7. A pharmaceutical composition containing a peptide comprising the following amino acid sequence: or the pharmaceutically-acceptable salts thereof and a pharmaceutically-acceptable carrier.

8. A pharmaceutical composition containing a the peptide comprising the following amino acid sequence:

Glu—Asp—Asn—Cys—Ileu—Ala—Glu—Asp—Tyr—Gly—Lys—

Cys—Thr—Trp—Gly—Gly—Thr—Lys—Cys—Cys—Arg—Gly—

Arg—Pro—Cys—Arg—Cys—Ser—Met—Ileu—Gly—Thr—Asn—

Cys—Glu—Cys—Thr—Pro—Arg—Leu—Ileu—Met—Glu—Gly—

Leu—Ser—Phe—Ala—OH$_x$ or the pharmaceutically-acceptable salts thereof and a pharmaceutically-acceptable carrier.

* * * * *

UNITED STATES PATENT AND TRADEMARK OFFICE
CERTIFICATE OF CORRECTION

PATENT NO. : 5,281,693  Page 1 of 2
DATED : January 25, 1994
INVENTOR(S) : J. R. HUNTER JACKSON, et al.

It is certified that error appears in the above-indentified patent and that said Letters Patent is hereby corrected as shown below:

Column 1, line 41, "side-effects" should be --side effects--
Column 1, line 56, "affect" should be --effect--
Column 1, line 58, after "channels" insert --.--
Column 5, line 9, after "employed" insert --within the scope of the present invention in order to facilitate--
Column 12, line 7, after "FIG. 1" insert --.--
Column 15, line 61, delete "it"
Column 16, lines 21-22, "naturally-occurring" should be --naturally occurring--
Column 16, line 55, "naturally-occurring" should be --naturally occurring--
Column 17, line 1, after "can" insert --be--
Column 17, line 2, after "Phe" insert --,--
Column 17, line 4, "neutral," should be --neutral;--
Column 17, line 5, "nonpolar," should be --nonpolar;--.
Column 17, line 5, "acidic," should be --acidic;--
Column 17, line 31, after "synaptic" insert --transmission using the electrophysiological methods described below--
Column 18, line 26, "Was" should be --was--
Column 19, line 60, after "bromide" insert --.--
Column 20, line 25, after "primers" insert --.--

UNITED STATES PATENT AND TRADEMARK OFFICE
CERTIFICATE OF CORRECTION

PATENT NO. : 5,281,693
DATED : January 25, 1994
INVENTOR(S) : J. R. HUNTER JACKSON et al.

It is certified that error appears in the above-indentified patent and that said Letters Patent is hereby corrected as shown below:

Column 24, line 12, before "or" insert the following:
-- Glu-Asp-Asn-Cys-Ileu-Ala-Glu-Asp-Tyr-Gly-Lys-
Cys-Thr-Trp-Gly-Gly-Thr-Lys-Cys-Cys-Arg-Gly-
Arg-Pro-Cys-Arg-Cys-Ser-Met-Ileu-Gly-Thr-Asn-
Cys-Glu-Cys-Thr-Pro-Arg-Leu-Ileu-Met-Glu-Gly-
Leu-Ser-Phe-Ala --

Column 24, lines 12 and 13, "pharmaceutically-acceptable" should be --pharmaceutically acceptable--
Column 24, line 14, delete "the"
Column 24, line 25, "$OH_x$" should be --OH--.
Column 24, lines 27 and 28, "pharmaceutically-acceptable" should be --pharmaceutically acceptable--

Signed and Sealed this

Third Day of January, 1995

Attest:

BRUCE LEHMAN

*Attesting Officer*        *Commissioner of Patents and Trademarks*